US008403138B2

(12) United States Patent
Weisshaupt et al.

(10) Patent No.: US 8,403,138 B2
(45) Date of Patent: Mar. 26, 2013

(54) SURGICAL CLIP CARTRIDGE AND HOUSING MEMBER FOR USE THEREIN

(75) Inventors: Dieter Weisshaupt, Immendingen (DE); Alexander Disch, Freiburg (DE)

(73) Assignee: Aesculap AG, Tuttlingen (DE)

( * ) Notice: Subject to any disclaimer, the term of this patent is extended or adjusted under 35 U.S.C. 154(b) by 244 days.

(21) Appl. No.: 12/924,370

(22) Filed: Sep. 23, 2010

(65) Prior Publication Data

US 2011/0087244 A1 Apr. 14, 2011

Related U.S. Application Data

(63) Continuation of application No. PCT/EP2008/009848, filed on Nov. 21, 2008.

(30) Foreign Application Priority Data

Apr. 10, 2008 (DE) .................. 10 2008 018 158

(51) Int. Cl.
*A61B 17/10* (2006.01)
(52) U.S. Cl. ........................................ 206/340
(58) Field of Classification Search .................. 206/340, 206/341, 480, 481, 482, 477, 807
See application file for complete search history.

(56) References Cited

U.S. PATENT DOCUMENTS

| 3,363,628 A | 1/1968 | Wood |
| 4,146,130 A | 3/1979 | Samuels et al. |
| 4,696,396 A | 9/1987 | Samuels |
| 4,936,447 A * | 6/1990 | Peiffer ......................... 206/339 |
| 4,961,499 A | 10/1990 | Kulp |
| 5,441,509 A | 8/1995 | Vidal et al. |
| 6,158,583 A | 12/2000 | Forster |
| 6,273,253 B1 | 8/2001 | Forster et al. |
| 6,460,700 B2 | 10/2002 | Weisshaupt |
| 6,880,699 B2 * | 4/2005 | Gallagher ...................... 206/339 |
| 2002/0017472 A1 | 2/2002 | Weisshaupt |
| 2002/0046961 A1 | 4/2002 | Levinson et al. |
| 2006/0124485 A1 | 6/2006 | Kennedy |
| 2006/0212049 A1 * | 9/2006 | Mohiuddin ................... 606/151 |
| 2008/0312670 A1 | 12/2008 | Lutze et al. |

FOREIGN PATENT DOCUMENTS

| DE | 690 29 474 | 7/1997 |
| DE | 199 03 752 | 3/2000 |
| DE | 101 05 235 | 8/2002 |
| DE | 697 13 608 | 2/2003 |
| DE | 20 2006 011 054 | 9/2006 |
| DE | 10 2006 001 344 | 7/2007 |
| DE | 20 2007 007 097 | 8/2007 |
| DE | 20 2008 004 929 | 7/2008 |
| EP | 0 494 243 | 12/1996 |

* cited by examiner

*Primary Examiner* — Steven A. Reynolds
*Assistant Examiner* — Kim M Chu
(74) *Attorney, Agent, or Firm* — Lipsitz & McAllister, LLC

(57) ABSTRACT

In order to improve the fixing of the surgical clips in the housing member in a surgical clip cartridge with a housing member and with a plurality of C-shaped surgical clips stored therein, having two limbs connected to one another by a web, the housing member comprising a plurality of compartments each to receive a surgical clip, with a support face adapted to the contour of the surgical clip in each compartment, against which support face a respective surgical clip abuts with its inner face, with holding members arranged on the housing member, which can be pivoted from a holding position into a release position and, in the holding position, fix the surgical clip in its compartment and, in the release position, are removed from the surgical clip, it is proposed that openings are provided in the limbs, in which the holding members engage in the holding position.

12 Claims, 13 Drawing Sheets

SURGICAL CLIP CARTRIDGE AND HOUSING MEMBER FOR USE THEREIN

This application is a continuation of international application number PCT/EP 2008/009848 filed on Nov. 21, 2008 and claims the benefit of German Patent application no. DE 10 2008 018 158.7 filed on Apr. 10, 2008.

The present disclosure relates to the subject matter disclosed in international application PCT/EP 2008/009848 of Nov. 21, 2008 and German patent application DE 10 2008 018 158.7 of Apr. 10, 2008, which are incorporated herein by reference in their entirety and for all purposes.

BACKGROUND OF THE INVENTION

The invention relates to a surgical clip cartridge with a housing member and with a plurality of C-shaped surgical clips stored therein having two limbs connected to one another by a web, the housing member comprising a plurality of compartments each for receiving a surgical clip, with a support face adapted to the contour of the surgical clip in each compartment, against which support face a respective surgical clip abuts with its inner face, and with holding members arranged on the housing member, which can be pivoted from a holding position into a release position and, in the holding position, fix the surgical clip in its compartment and, in the release position, are removed from the surgical clip.

A surgical clip cartridge of this type is known, for example, from EP 0 494 243 B1. A plurality of surgical clips can be stored next to one another in a magazine of this type and can be removed by means of a removal tool. The surgical clips are stored in the compartments abutting on a support face and are fixed in this position by holding members pressed on to the outer sides of the limbs. However, this fixing takes place exclusively by means of a frictional connection, so that there is a risk of a surgical clip being unintentionally released from the support face and then adopting an undefined position in the compartment of the housing member. Therefore there is a risk of a surgical clip not being able to be correctly gripped by a removal tool and, in the worst case, a surgical clip could also fall out of the magazine.

A surgical clip cartridge is described in DE 101 05 235 A1, in which the surgical clips are held on the housing member by projections engaging in transverse grooves on the outer side of the surgical clips.

The object of the invention is to configure a surgical clip cartridge of the above-mentioned type in such a way that the surgical clips are particularly reliably fixed therein until they are removed.

SUMMARY OF THE INVENTION

This object is achieved according to the invention in a surgical clip cartridge of the type described at the outset in that openings, in which the holding members engage in the holding position, are provided in the limbs, and in that the opening in the limb of the surgical clip is a slot running along the limbs.

This configuration produces a fixing of the surgical clips on the support faces by a positive connection and, in the holding position, the holding members engage in the openings and thereby ensure that the surgical clip cannot unintentionally be displaced from the storage position, in which it abuts the support face. As the opening in the limb of the surgical clip is a slot running along the limbs, a particularly secure fixing of the surgical clip is produced by the holding members entering the slot-like opening and the positive connection occurring in the process.

In a preferred embodiment it is provided that the holding members, on their upper side, bear a sliding face for a removal tool, with which the latter comes onto contact on displacement along the limbs of a surgical clip and thereby pivots the holding members out of the holding position into the release position. The release of the surgical clips is thus brought about merely by introducing the removal tool and the user does not therefore have to provide any particular steps to release the surgical clips, it merely being necessary to apply the removal tool to the outer sides of the limbs of the surgical clip.

In this case, it may in particular be provided that the holding members are formed as strips in their region engaging in the opening and abut with their side walls against the lateral edges of the opening. The holding members therefore not only hold the surgical clips in the bearing position, they also orient them relative to the housing member in that the strip-like holding members engage in the slot-like openings and abut with their side faces against the side edges thereof. This ensures an exact setting of the surgical clips in the housing member.

In a preferred embodiment, it can be provided that an opening, into which a projection of the support face projects when the surgical clip abuts the support face, is also arranged in the web of the surgical clip. This projection is also used for the precise positioning of the surgical clip on the support face and it prevents a lateral displacement of the surgical clip on the support face.

With this opening in the web of the surgical clip, it may also be provided that this opening is a slot running along the limbs.

The projection may also be formed as a strip in this case and abut with its side walls against the lateral edges of the opening in the web of the surgical clip.

It is particularly favourable if the housing member is configured in one piece with the support faces and the holding members; in particular, it may consist of a preferably sterilisable plastics material.

It is advantageous here if the holding members are connected by a bending web to the housing member which is permanently plastically deformed when the holding members are pivoted out of the holding position into the release position. After pivoting out into the release position, the holding members thus remain in this release position and therefore give an indication that the surgical clip has been removed from the corresponding compartment, in which the holding members are pivoted out. In the configuration of the bearing body made of plastics material, the bending web may, for example, be configured in such a way that when the holding members are pivoted out, a so-called "stress whitening" occurs in the material, in other words a plastic deformation of the plastic material, which is permanent.

In a particularly preferred configuration it is provided that the surgical clip has two longitudinal webs running at a spacing from one another, which are connected to another by a transverse web at the ends of the limbs and which, between them, define a slot-shaped intermediate space, which forms the openings in the limbs and optionally in the web of the surgical clip in which the holding members or the projection of the support face engage. Surgical clips of this type with two longitudinal webs running parallel to one another are known per se and are particularly suitable for use in a housing member of the type described, in which the holding members, in the holding position, engage in the intermediate space between the longitudinal webs and in which a projection on the support face optionally also engages in the intermediate space between the longitudinal webs.

It is particularly advantageous if the openings of the limbs and the openings in the web of the surgical clip are separated from one another by further transverse webs connecting the longitudinal webs of the surgical clip. These transverse webs give the surgical clip an additional dimensional stability and contribute to the surgical clips being able to be particularly reliably gripped by a removal tool.

It may be provided that the holding members are fixed in their holding position relative to the housing member by a releasable, resilient latching connection. This ensures that the holding members cannot be unintentionally pivoted out of their holding position into the release position and pivoting is only possible when the holding members are pivoted by introduction of the removal tool with a defined force which releases the resilient latching connection.

For this purpose, the holding member may, for example, carry at least one lateral latching projection which engages in a latching recess of the housing member.

This bearing recess is preferably arranged in a partition separating two adjacent compartments of the housing member. These partitions also have the advantage that the removal tool is laterally guided on introduction into a compartment.

In a first preferred embodiment it is provided that the holding members are arranged on the outside of the surgical clip, in that they are pivoted in, in their holding position, in the direction of the centre of the surgical clip and enter the opening of the limbs from the outside to the inside, while, in the release position, they are pivoted outwardly away from the surgical clip.

However, a modified configuration is also possible, in which it is provided that the holding members are arranged on the inner side of the surgical clip in that, in their holding position, they are pivoted out in the direction away from the centre of the surgical clip and enter the opening of the limbs from the inside to the outside, while, in the release position, they are pivoted inwardly towards the centre of the surgical clip.

The following description of preferred embodiments of the invention, in conjunction with the drawings, is used for more detailed description.

DETAILED DESCRIPTION OF THE INVENTION

Figure 1:
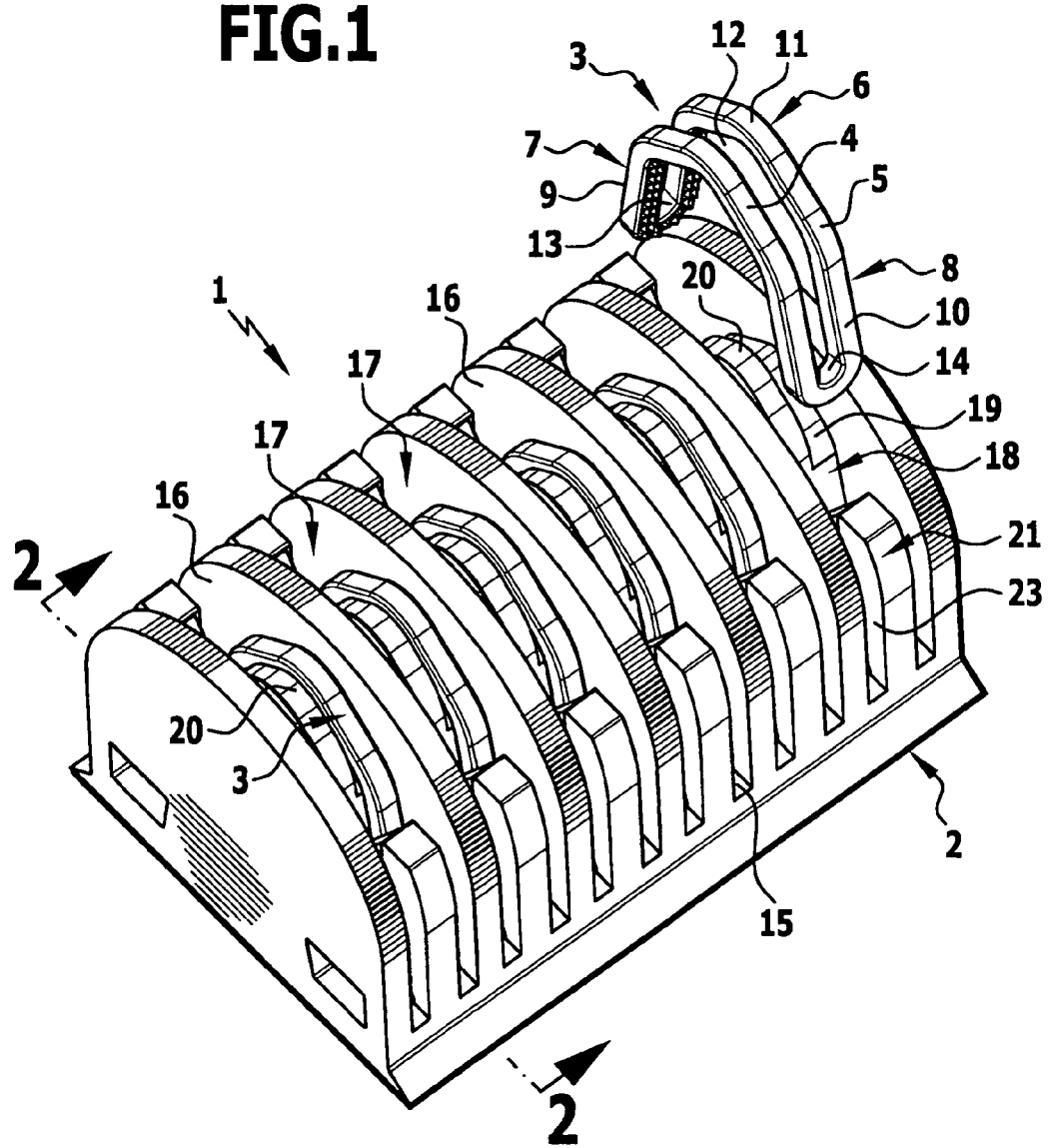
FIG. 1 is a perspective view of a surgical clip cartridge with five surgical clips inserted therein and one surgical clip removed from a compartment of the housing member.
Figure 2:
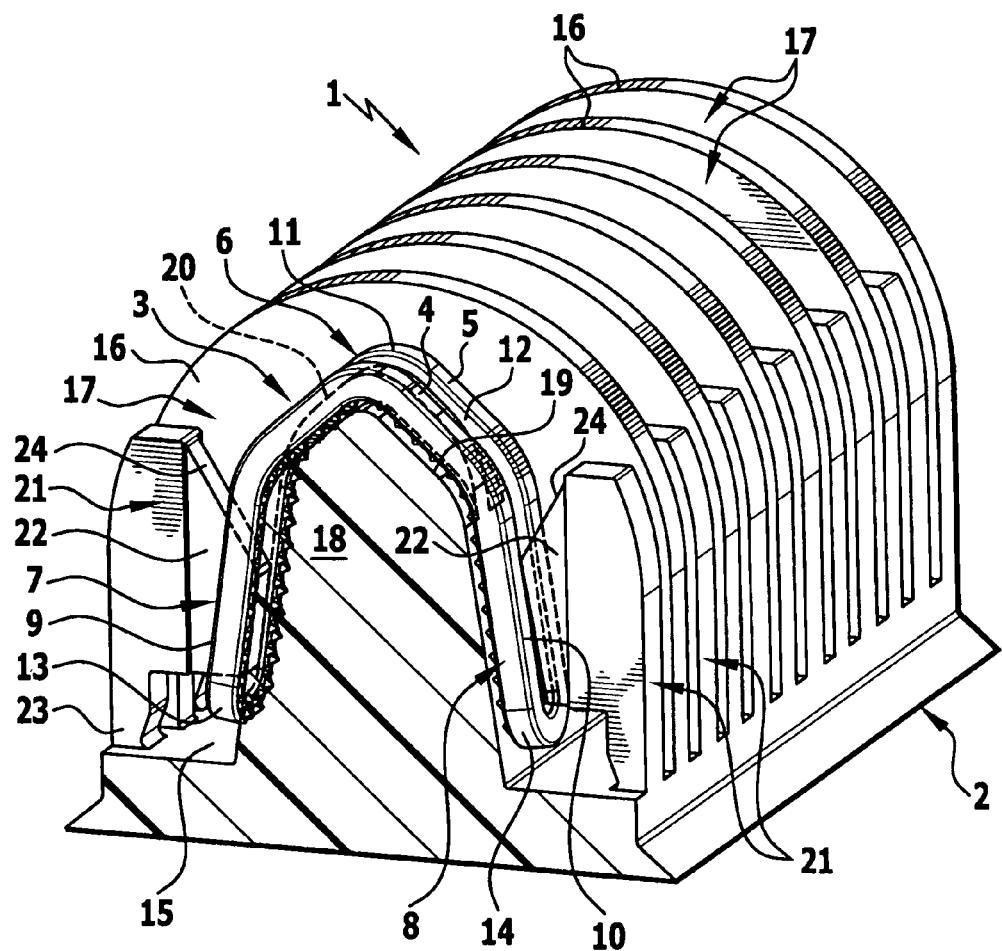
FIG. 2: is a perspective view of the surgical clip cartridge cut along the line 2-2 of FIG. 1 with a surgical clip inserted in the foremost compartment.
Figure 3:
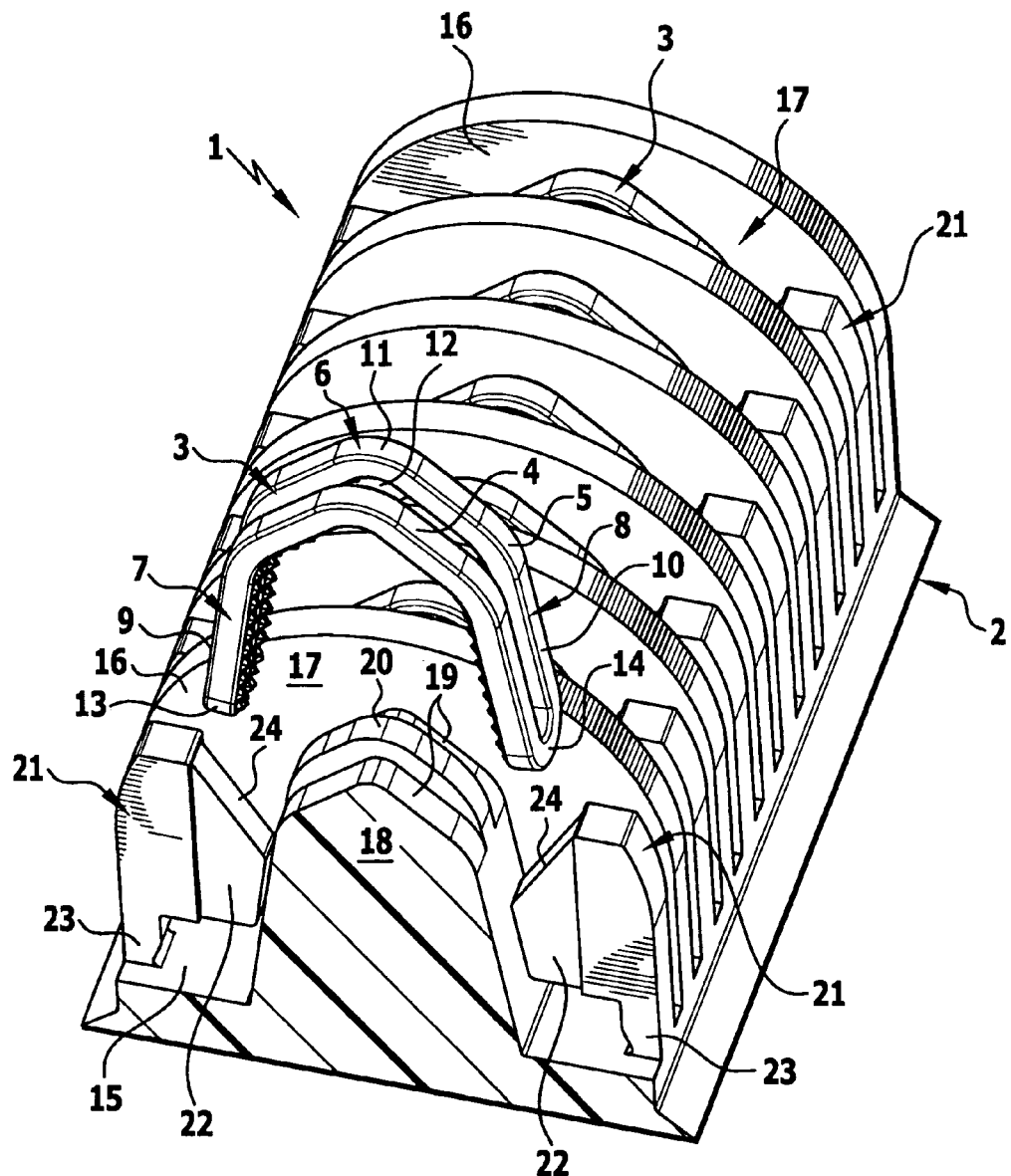
FIG. 3: is a view similar to FIG. 2 with the foremost compartment without an inserted surgical clip and with a separate surgical clip.

The surgical clip cartridge 1 shown in FIGS. 1 to 10 comprises a housing member 2 in which a number of surgical clips 3 is inserted. The surgical clip 3 is substantially C-shaped with two limbs 7, 8 connected to one another by a web 6. In the embodiment shown, the limbs 7, 8 are substantially flat and slightly diverge toward their free ends; on the other hand, the web 6 is V-shaped with two flat portions 9, 10 and a sharp bend 11 between the flat portions 9, 10.

An opening 12 in the form of a slot runs in the surgical clip 3 over the major part of the length of the limbs 7, 8 and over the entire web 6, so that the surgical dip 3 can also be regarded as a clamp consisting of two longitudinal webs 4, 5 extending parallel to one another, which are connected to one another at the free ends of the limbs 7, 8 in the form of bent transverse webs 13, 14.

The housing member 2 has a rectangular base plate 15, from which a plurality of flat vertical partitions 16 extending parallel to the narrow side of the base plate 15 protrude, said partitions being semi-circularly delimited at their upper side and separating off compartments 17 between them. Arranged in each such compartment 17, starting from the base plate 15, is a support body 18 which extends upwardly between the two partitions 16 and the outer contour of which is substantially adapted to the inner contour of a surgical clip 3, so that the outer face of the support body 18 forms a support face 19, on which a surgical clip 3 can be placed in such a way that it abuts with its web 6 and with its limbs 7 against this support face 19.

The support face 19, at its upper end, carries a projection 20 which is formed as a strip and which engages in the region of the web 6 in the opening 12, in other words in the space between the two longitudinal webs 4, 5 of the surgical clip 3 running next to one another, so that a surgical clip 3 placed on the support face 19 is thereby secured against a lateral displacement. The projection 20 is preferably as wide as the space between the longitudinal webs 4, 5, so that by the strip-like projection 20 engaging in the opening 12, an orientation of the surgical clip 3 on the support body 18 also takes place.

Formed in each compartment 17 in the region of the longitudinal edge of the base plate 15 on opposing sides of the compartment 17 are two holding members 21 which each carry an inwardly pointing, strip-like projection 22 which engages in the region of the limbs 7, 8 in the opening 12 of a surgical clip 3 placed on the support face 19. The dimensions are selected such that this strip-like projection 22 abuts with its side faces against the side edges of the opening 12 and therefore also contributes to an orientation of the surgical clip 3. This projection 22 also rests on the transverse webs 13 or 14 of the two limbs 7 and therefore prevents it being possible for the surgical clip 3 to be unintentionally lifted from the support face 19.

The holding members 21 are connected to the base plate 15 by a bending web 23 with a relatively small cross section and are normally configured in such a way that with their outer contour they are aligned with the outer contour of the partitions 16 and in the process engage with the projection 22 in the opening 12. In this position, the holding members 21 therefore hold the surgical clip 3 on the support body 18. This position of the holding members 21 is therefore called the holding position.

On the upper side, the projections 22 have a sliding face 24 dropping away obliquely from the outside to the inside, which projects laterally, at least partially, over the surgical clip 3 in the holding position, so that clamping jaws 25, 26 of a removal tool can be placed on this region (FIG. 4) when these clamping arms 25, 26 are inserted from above into a compartment 17 along the limbs 7, 8. In this case, the clamping arms 25, 26 are applied to the outer side of the limbs 7, 8 and simultaneously pivot the holding members 21 outwardly during further insertion. During this pivoting movement the bending web 23 is plastically deformed, so that this pivoting movement of the holding members is irreversible. During the pivoting out movement, the projections 22 leave the opening 12 and thereby release the surgical clip 3

In addition, reference is made to the fact that owing to the oblique sliding faces 24, the insertion of the clamping arms 25, 26 is also facilitated as the sliding faces 24 simultaneously exert a centring function on the two clamping arms 25, 26 and guide these into the correct resting position on the limbs 7, 8.

Figure 4:
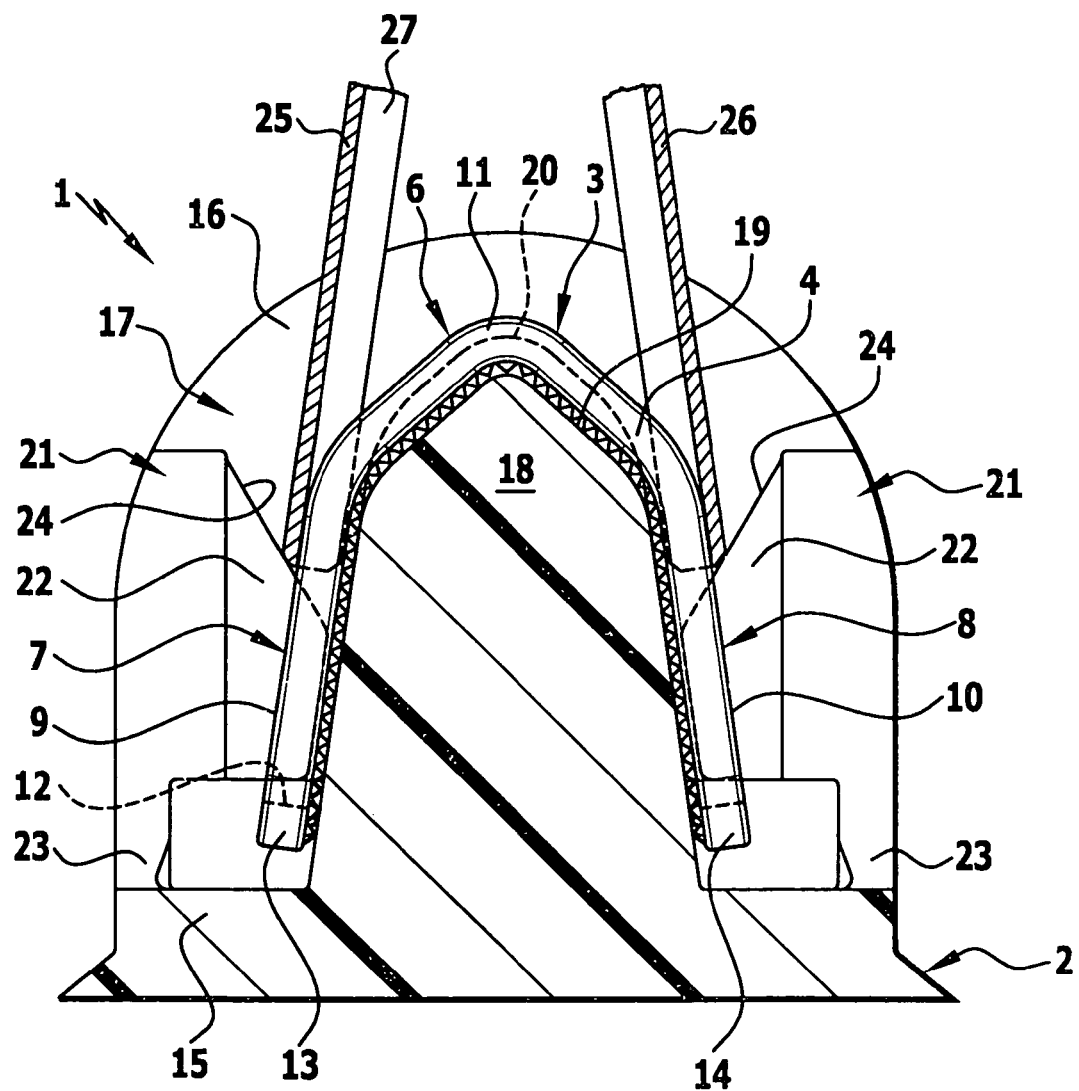
FIG. 4: is a sectional view of the surgical clip cartridge of FIG. 1 along the line 2-2 in FIG. 1 with two clamping arms of a removal tool applied to a surgical clip at the beginning of the introduction of the clamping arms.
Figure 5:
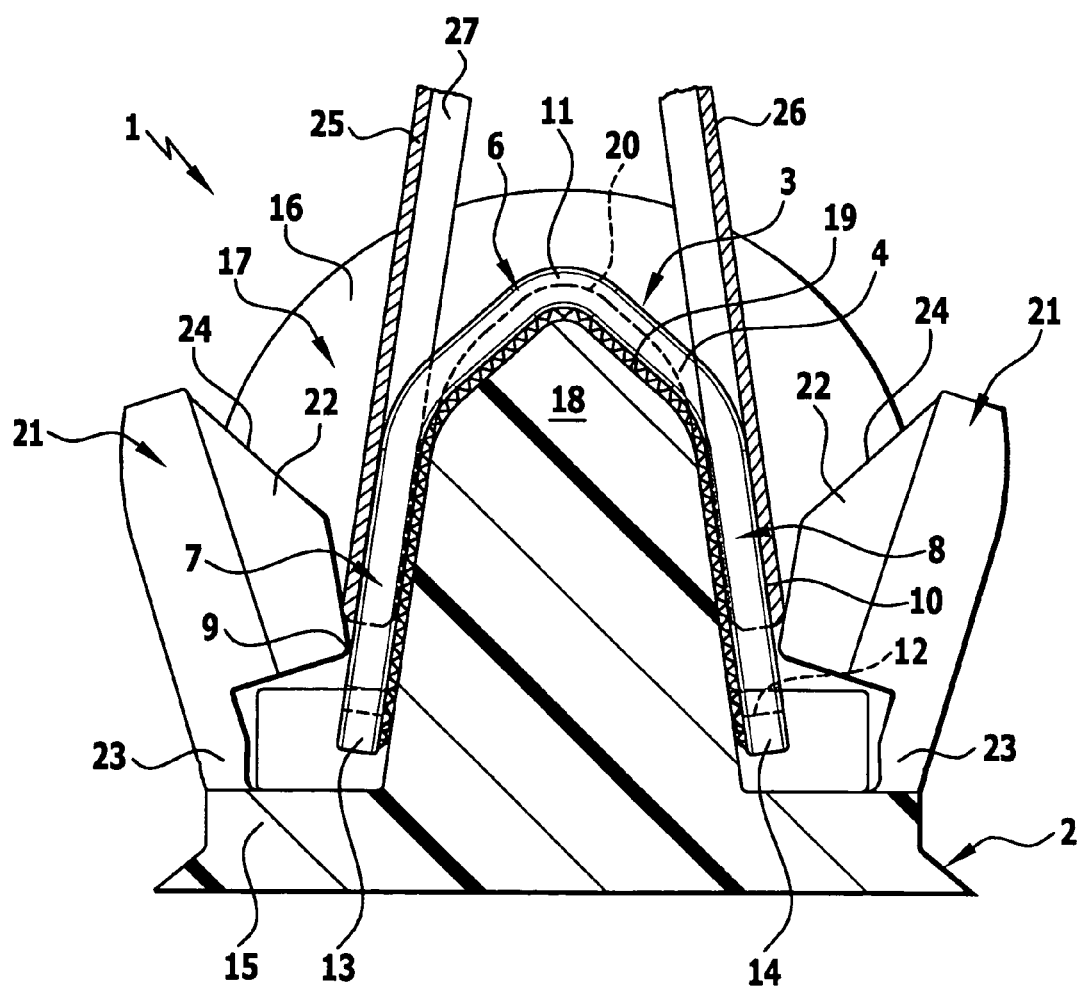
FIG. 5: is a view similar to FIG. 4 with clamping arms pushed forward along the limbs of the surgical clip and the holding members pivoted out.
Figure 6:
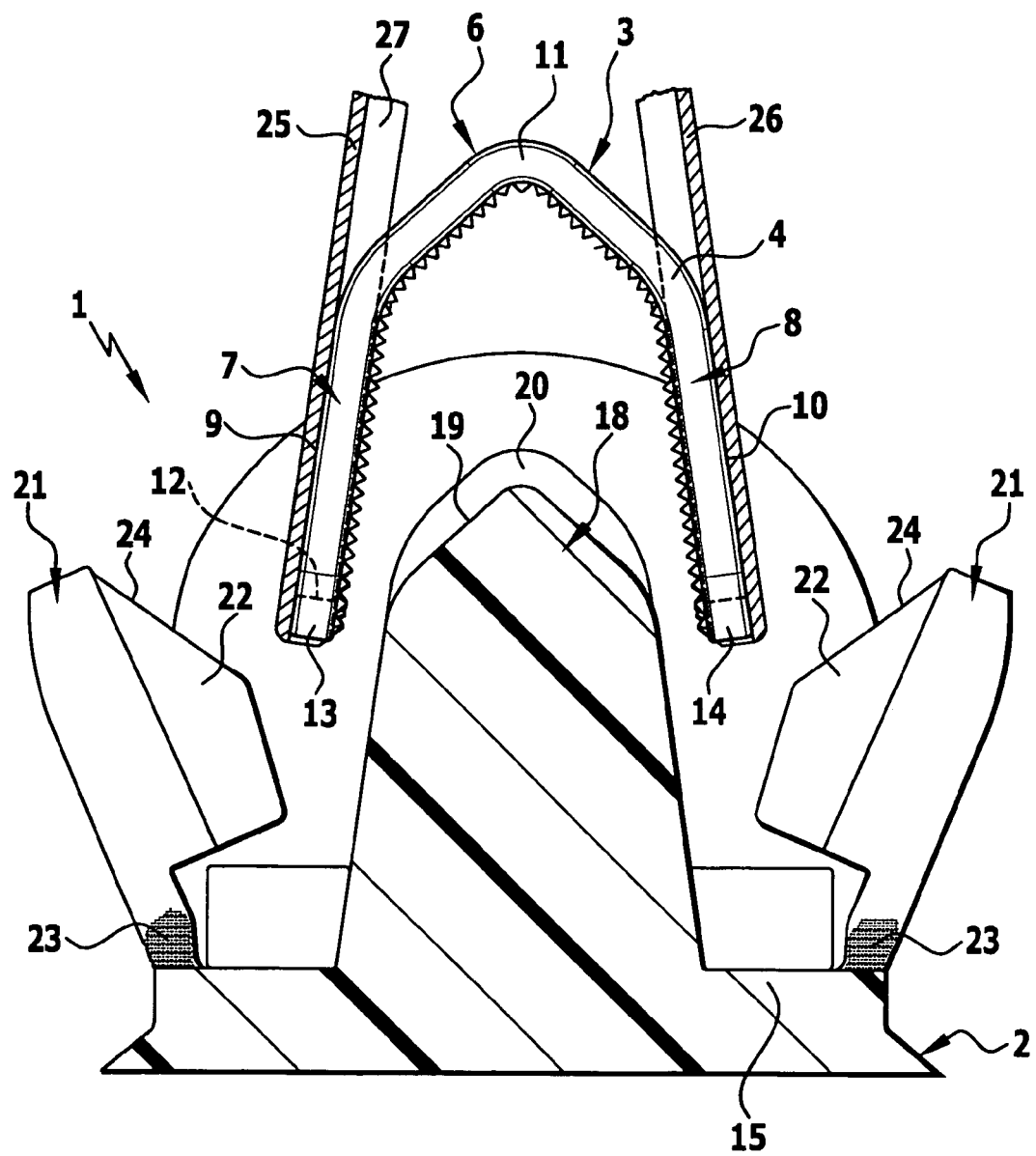
FIG. 6: is a view similar to FIG. 5 with holding members completely pivoted out and during the removal of the surgical clip by means of the removal tool.
Figure 7:
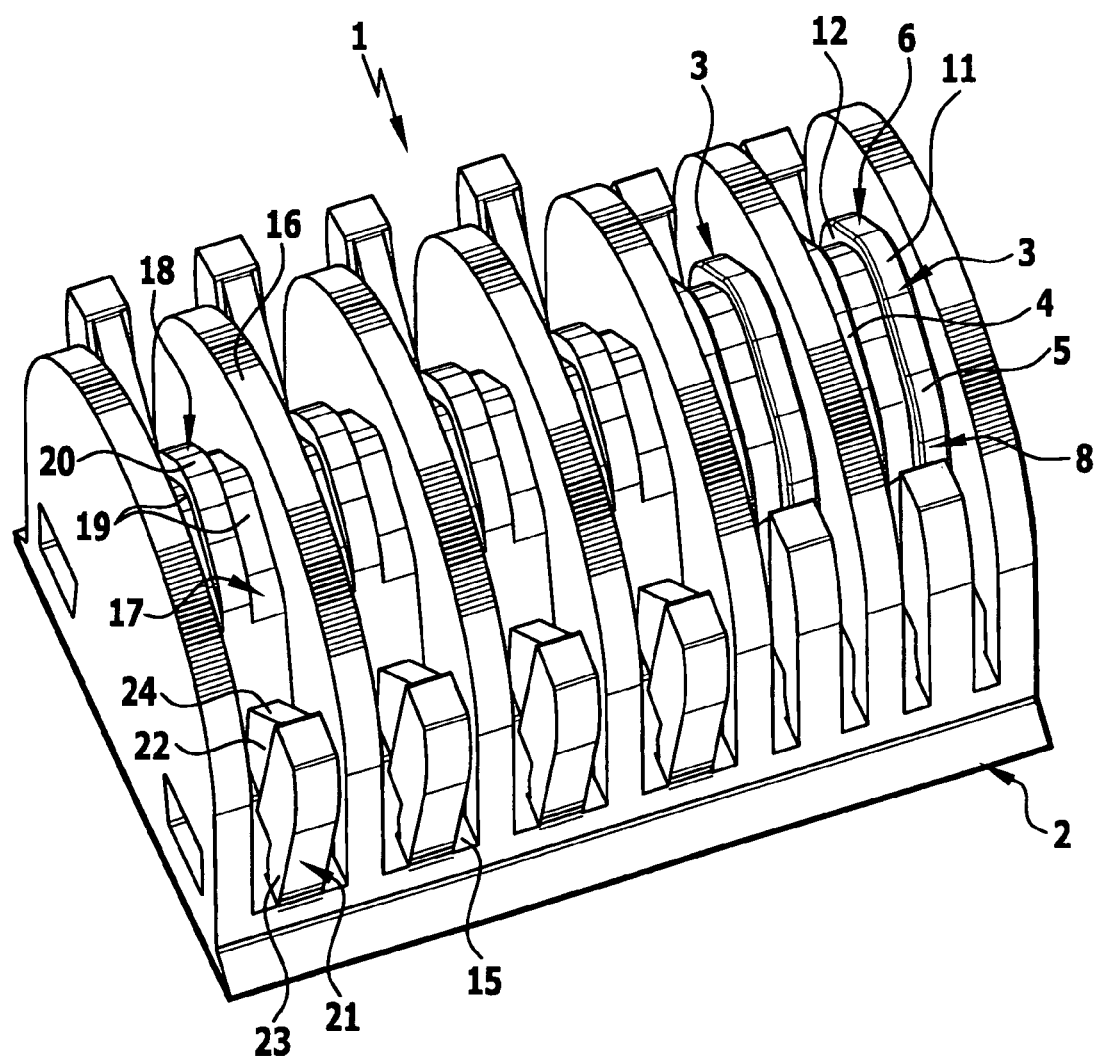
FIG. 7: is a perspective view of the surgical clip cartridge of FIG. 1 with surgical clips in two compartments and with four empty compartments after the removal of the surgical clips.

On their inner sides, the clamping arms 25, 26 carry a strip-like projection 27, which, when the clamping arms 25, 26 are pushed forward on the limbs 7, 8, enters the opening 12 and therefore aligns the surgical clip 3 relative to the clamping arms 25, 26 (FIGS. 4 and 5).

As soon as the clamping arms 25, 26 have been completely inserted into the compartment 17, they contact the entire area of the outer side of the limbs 7, 8 and have pivoted the holding members 21 fully outwardly. The surgical clip 3 is now held in frictional contact on the clamping arms 25, 26 by the areal contact, but is no longer fixed by the holding members 21 relative to the housing member 2. When the clamping arms 25, 26 are withdrawn from the compartment 17, the surgical clip 3 clamped between the clamping arms 25, 26 can therefore be removed from the compartment 17 and transferred by means of the removal tool to the site of use.

After the removal of a surgical clip 3 from the compartment, the holding members 21 of this compartment are in the pivoted-out position, in which they project laterally over the outer contour of the housing member 2 defined by the partitions 16, and the user is therefore given an indication that the surgical clip 3 has already been removed from this compartment.

While the surgical clips 3 generally consist of a body-compatible metal, for example titanium or a titanium alloy, it is advantageous to produce the housing member 2 in one piece from a preferably sterilised plastics material, for example as an injection-moulded part. The support bodies 18 and the holding members 21 can thus be injected in one piece on the housing member 2 and the same applies with respect to the partitions 16.

Surgical clips 3, which have a single, continuous, slot-shaped opening 12 between the longitudinal webs 4, 5, are used in the embodiment of FIGS. 1 to 7.

Figure 8:
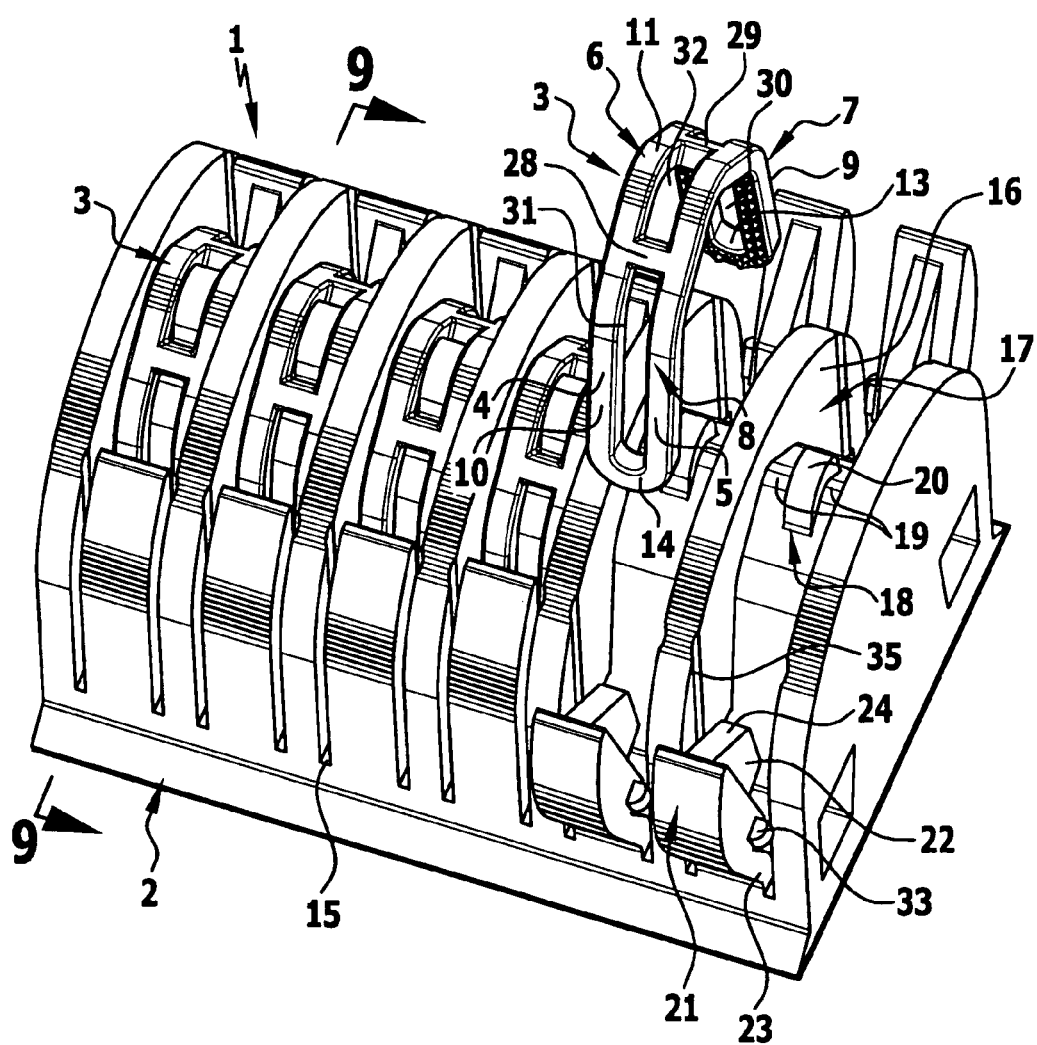
FIG. 8: is a perspective view of a further preferred embodiment of a surgical clip cartridge with surgical clips having additional transverse webs.
Figure 9:
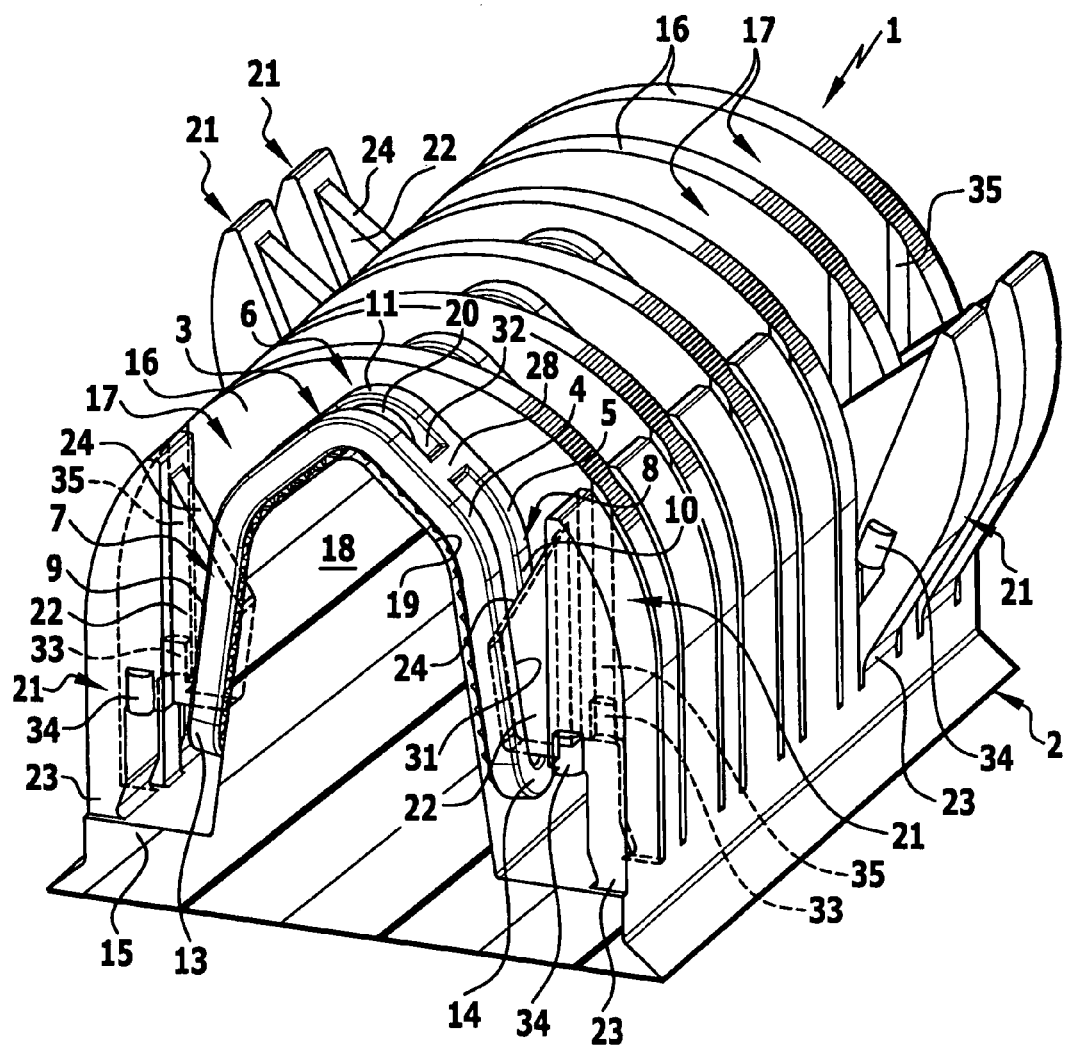
FIG. 9: is a perspective view of the surgical clip cartridge of FIG. 8 with a housing member cut along the line 9-9.
Figure 10:
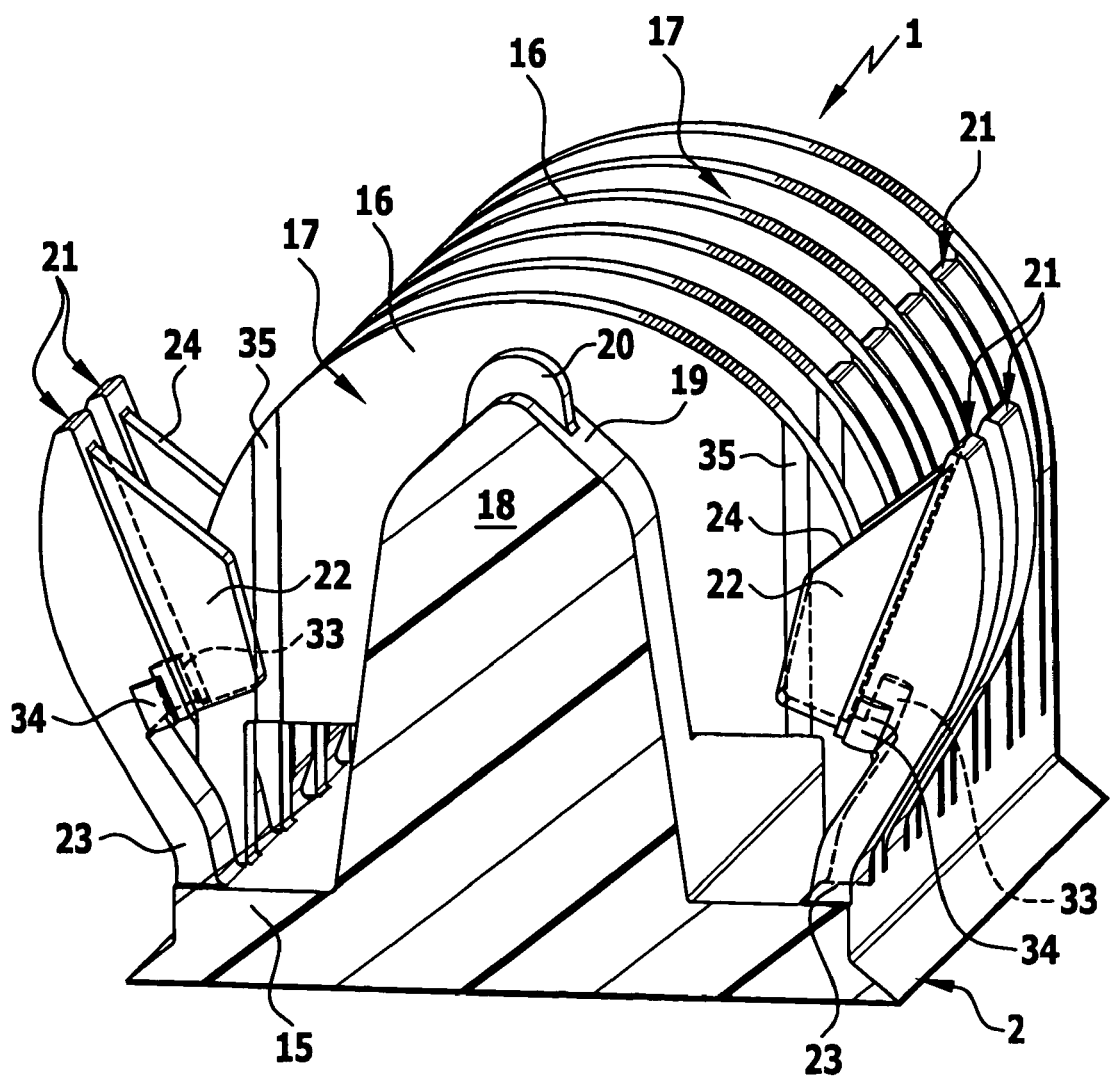
FIG. 10: is a perspective view of the surgical clip cartridge of FIG. 8 with a housing member cut along the line 10-10.

In contrast to this, surgical clips 3, in which the longitudinal webs 4, 5 are connected to one another by additional transverse webs 28, 29, are used in the embodiment of FIGS. 8 to 10, in which mutually corresponding parts have the same reference numerals. As a result, openings 30, 31 or 32, which are separate from one another, are produced, on the one hand, in the region of the limbs 7, 8 and, on the other hand, in the region of the web 6. Owing to these transverse webs 28, 29, the dimensional stability of the surgical clip 3 is increased and these transverse webs also contribute to the clamping arms 25, 26 being able to engage surgical clips of this type even more reliably through a clamping fit.

In accordance with the shorter length of the opening 32 in the web 6, the projections 20 on the support face 19 are also shorter in the embodiment of FIGS. 8 to 10 than in the embodiment of FIGS. 1 to 7.

In the embodiment of FIGS. 8 to 10 it is also provided that the holding members 21 on their side faces carry laterally projecting latching projections 33, 34, which engage in groove-like indentations 35 of the adjacent partitions 16 when the holding members 21 are pivoted into the holding position and therefore form a releasable, resilient latching connection, by means of which, the holding members 21 are fixed in their holding position. This increases the reliability of the fixing of the surgical clips 3 in the housing member 2 and this latching connection can only be released in that the holding members 21 are pivoted out by means of the clamping arms 25, 26.

Figure 11:
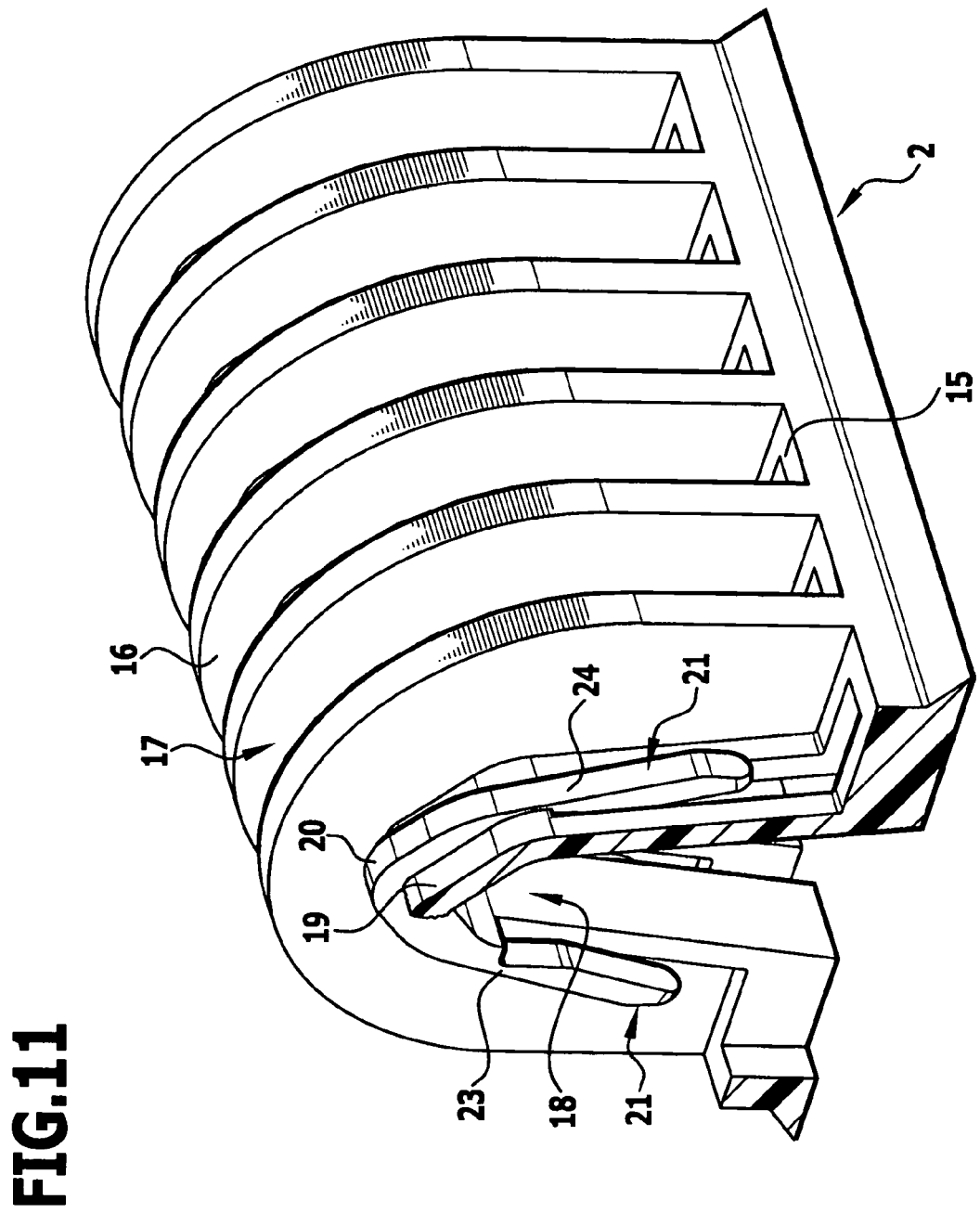
FIG. 11: is a perspective view of a further preferred embodiment of a surgical clip cartridge with holding members pivoted inward from the holding position into the release position.
Figure 12:
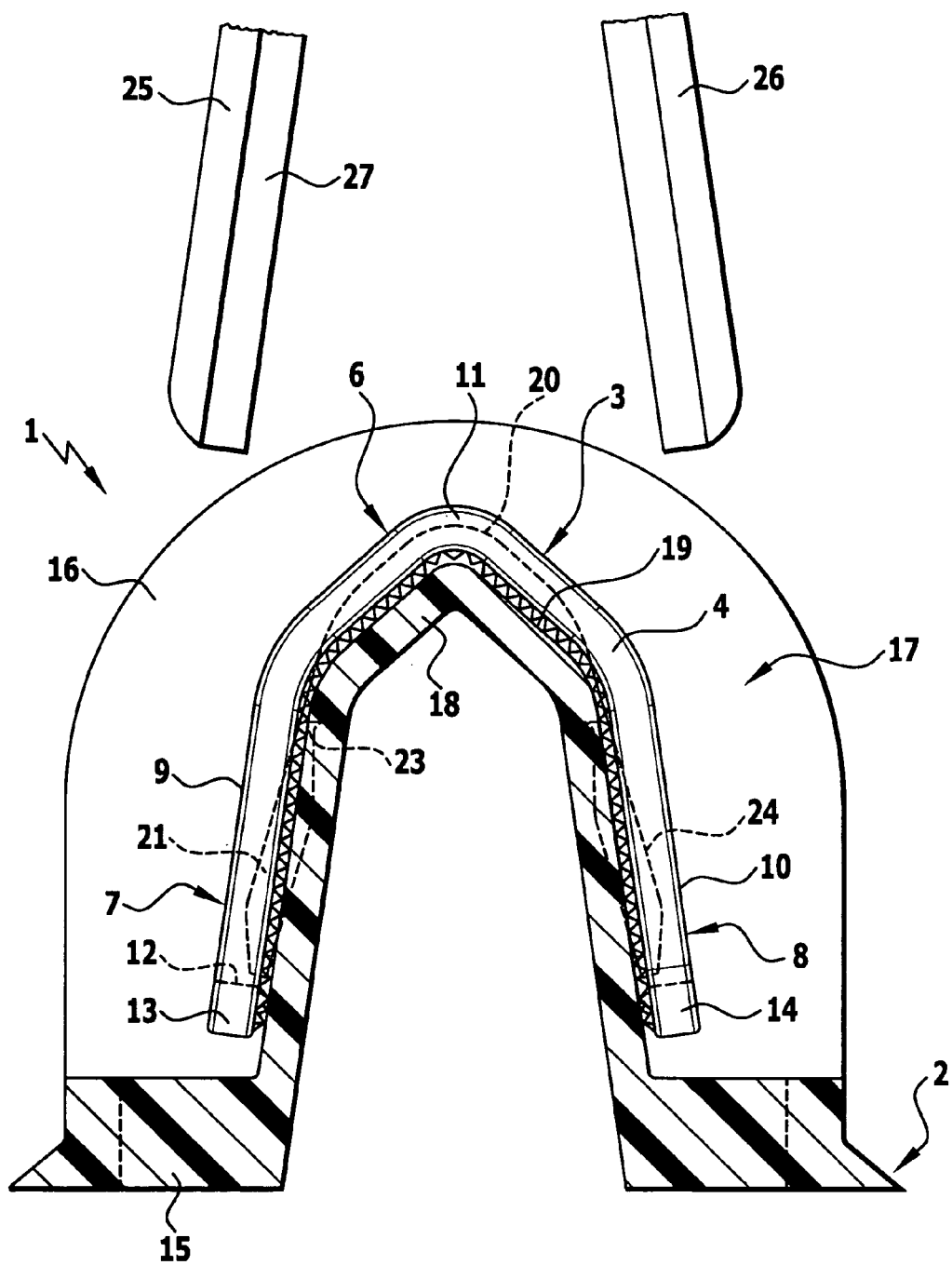
FIG. 12: is a sectional view of the surgical clip cartridge of FIG. 11 along the line 12-12 with the holding members in the holding position and before the application of a removal tool
Figure 13:
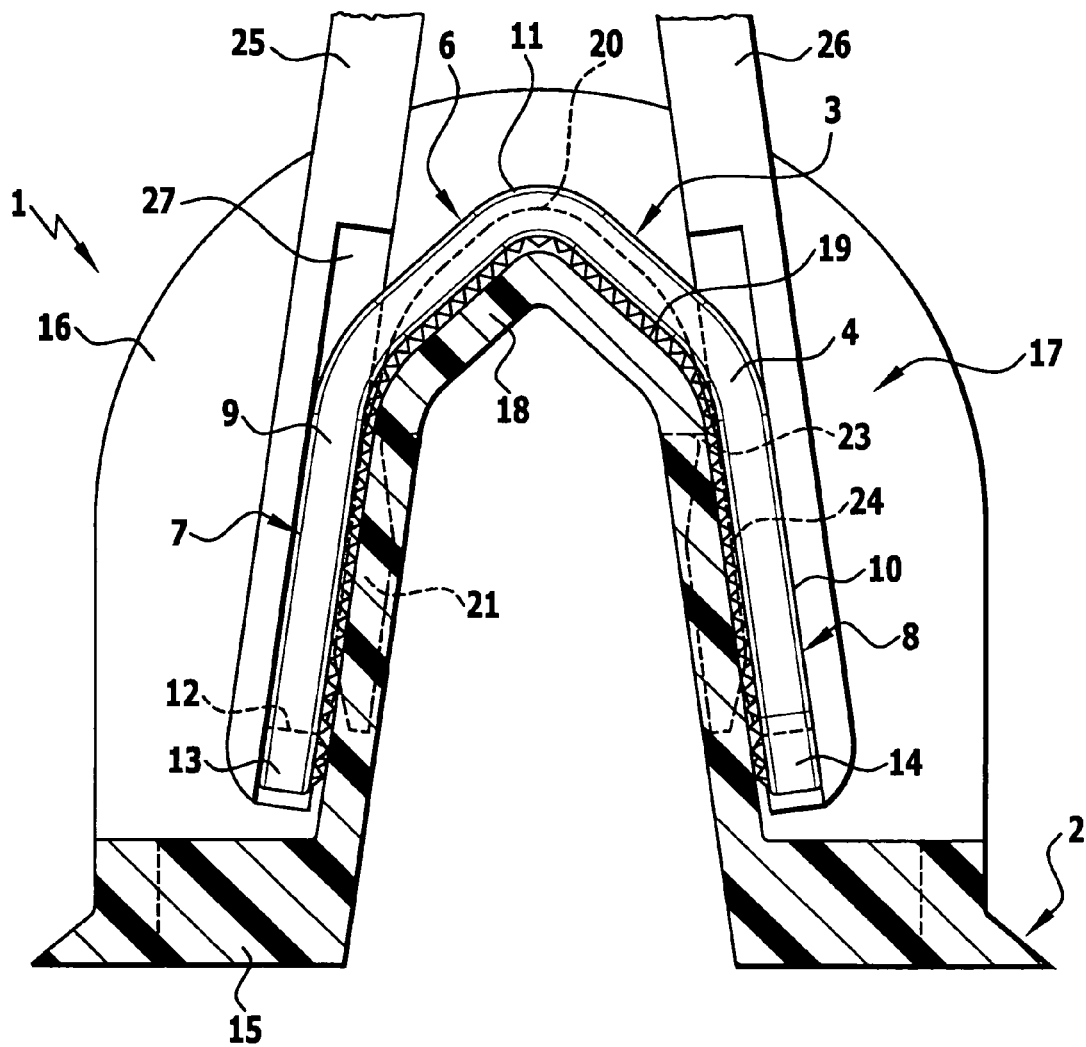
FIG. 13: is a view similar to FIG. 12 with a removal tool applied on the outer side of the surgical clip and holding members pivoted inward into the release position.

The embodiment of FIGS. 11 to 13 is constructed similarly to the embodiments of FIGS. 1 to 10 and corresponding parts therefore have the same reference numerals.

While the holding members 21 are arranged on the outside of the surgical clip 3 in the embodiment according to FIGS. 1 to 10 and, in their holding position, enter the slot-shaped opening 12 of the surgical clip 3 from the outside to the inside with the strip-shaped projection 22, in the embodiment of FIGS. 11 to 13, the arrangement of the holding members 22 is displaced to the inside of the surgical clip 3, in other words the holding members 22 are arranged directly adjacent to the support face 19 in such a way that they are only connected at their upper end by a bending web 23 to the support face 19, while their lower ends are free ends. In the holding position (FIG. 12), the holding members 21 are pivoted outwardly relative to the support face 19 and thus enter the slot-like opening 12 of the surgical clip 3 from the inside to the outside. When the clamping arms 25, 26 of the removal tool are applied to the outer side of the surgical clip 3, these clamping arms 25, 26 slide on the outer side of the pivoted-out holding members 21 into the holding position and thereby pivot the holding members 21 inwardly until they leave the slot-like openings 12 and thus release the surgical clip 3 (FIG. 13). The outer sides of the holding members 21 therefore also form a sliding face 24 obliquely falling away, which, however, in this case, runs from top to bottom, obliquely from the inside to the outside. After this release of the surgical clip 3, it can be removed by means of the removal tool from the cartridge.

The configurations, which are described with the aid of the different embodiments, of the surgical clips, on the one hand, and of the housing member, on the other hand, can also be exchanged with one another and realised in different combinations on a surgical clip cartridge.

The invention claimed is:
1. A surgical clip cartridge comprising:
a housing member;
a plurality of C-shaped surgical clips stored in the housing member, the C-shaped surgical clips having two limbs connected to one another by a web;

a plurality of compartments provided on the housing member, each compartment being adapted for receiving a respective one of the surgical clips, and having a support face adapted to a contour of the surgical clip, such that an inner face of the respective surgical clip abuts the support face;

holding members arranged on the housing member, each of the holding members being adapted to be pivoted from a holding position into a release position and, in the holding position, the holding members fix the respective surgical clip in the respective compartment and, in the release position, the holding members are removed from the respective surgical clip;

wherein:
at least one opening is provided in the limbs, the holding members each engaging in one of the at least one opening in a corresponding one of the limbs in the holding position;

the at least one opening in the limbs of the surgical clip comprises at least one slot running along the limbs;

the housing member, the support face, and the holding members consist of a plastics material;

the holding members are connected by a bending web to the housing member; and the bending web is permanently plastically deformed when the holding members are pivoted out of the holding position into the release position.

2. A surgical clip cartridge according to claim 1, wherein:
the holding members bear, on an upper side thereof, a sliding face for a removal tool, said tool comes into contact with the sliding face when pushed forward along the limbs of the surgical clip and thereby pivots the holding members from the holding position into the release position.

3. A surgical clip cartridge according to claim 1, wherein the holding members are in a form of strips in a region engaging in the at least one opening and rest with side walls of the strips against lateral edges of the at least one opening.

4. A surgical clip cartridge according to claim 1, wherein:
one of the at least one openings is arranged in the web of the surgical clip, and a projection of the support face projects into the opening in the web when the surgical clip abuts the support face.

5. A surgical clip cartridge according to claim 3, wherein:
one of the at least one openings is arranged in the web of the surgical clip, and a projection of the support face projects into the opening in the web when the surgical clip abuts the support face.

6. A surgical clip cartridge according to claim 4, wherein the opening in the web of the surgical clip is a slot running along the web.

7. A surgical clip cartridge according to claim 6, wherein the projection is formed as a strip in a region engaging in the opening of the web and abuts with side walls against lateral edges of the opening.

8. A surgical clip cartridge according to claim 1, wherein the housing member is configured in one piece with the support faces and the holding members.

9. A surgical clip cartridge according to claim 1, wherein:
the surgical clip has two longitudinal webs extending next to one another at a spacing, the webs are connected to one another at ends of the limbs by a transverse web, a slot-like space is defined between the limbs which forms the at least one opening in the limbs and in the web of the surgical clip; and the holding members and/or a projection of the support face engages in the slot-like space.

10. A surgical clip cartridge according to claim 1, wherein:
the holding members are arranged on an outside of the surgical clip, the holding members are pivoted in, in their holding position, in a direction of a center of the surgical clip and enter the at least one opening of the limbs from the outside to an inside, and in the release position, the holding members are pivoted outwardly away from the surgical clip.

11. A surgical clip cartridge according to claim 3, wherein:
the holding members are arranged on an outside of the surgical clip, the holding members are pivoted in, in their holding position, in a direction of a center of the surgical clip and enter the at least one opening of the limbs from the outside to an inside, and in the release position, the holding members are pivoted outwardly away from the surgical clip.

12. A surgical clip cartridge comprising:
a housing member;

a plurality of C-shaped surgical clips stored in the housing member, the C-shaped surgical clips having two limbs connected to one another by a web;

a plurality of compartments provided on the housing member, each compartment being adapted for receiving a respective one of the surgical clips, and having a support face adapted to a contour of the surgical clip, such that an inner face of the respective surgical clip abuts the support face;

holding members arranged on the housing member, each of the holding members being adapted to be pivoted from a holding position into a release position and, in the holding position, the holding members fix the respective surgical clip in the respective compartment and, in the release position, the holding members are removed from the respective surgical clip;

wherein:
at least one opening is provided in the limbs, the holding members each engaging in one of the at least one opening in a corresponding one of the limbs in the holding position;

the at least one opening in the limbs of the surgical clip comprises at least one slot running along the limbs;

one of the at least one openings is a slot arranged in the web of the surgical clip; and a projection of the support face projects into the opening in the web when the surgical clip abuts the support face, the projection is formed as a strip in a region engaging in the opening of the web and abuts with side walls against lateral edges of the opening.

* * * * *